US008647385B2

(12) United States Patent
Boucher et al.

(10) Patent No.: US 8,647,385 B2
(45) Date of Patent: Feb. 11, 2014

(54) APPARATUS AND METHOD FOR TIBIAL FIXATION OF SOFT TISSUE

(75) Inventors: James Boucher, Warsaw, IN (US); Stephen M. Howell, Elk Grove, CA (US); James Marcinek, Warsaw, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 0 days.

(21) Appl. No.: 13/549,912

(22) Filed: Jul. 16, 2012

(65) Prior Publication Data
US 2012/0283832 A1 Nov. 8, 2012

Related U.S. Application Data

(60) Division of application No. 11/742,009, filed on Apr. 30, 2007, now Pat. No. 8,221,498, which is a division of application No. 10/874,915, filed on Jun. 23, 2004, now Pat. No. 7,211,111, which is a division of application No. 10/167,074, filed on Jun. 10, 2002, now Pat. No. 6,755,840, which is a division of application No. 09/616,544, filed on Jul. 14, 2000, now Pat. No. 6,482,232, which is a continuation of application No. 09/356,959, filed on Jul. 19, 1999, now Pat. No. 6,280,472, which is a continuation-in-part of application No. 08/900,602, filed on Jul. 23, 1997, now Pat. No. 5,931,869.

(51) Int. Cl.
A61F 2/08 (2006.01)
(52) U.S. Cl.
USPC ..................... 623/13.14; 606/321

(58) Field of Classification Search
USPC ..................... 623/11.11, 13.11–13.12, 13.14; 606/297, 321
See application file for complete search history.

(56) References Cited

U.S. PATENT DOCUMENTS

| 2,248,054 A | 7/1941 | Decker |
| 2,267,925 A | 12/1941 | Johnston |
| 2,570,465 A | 10/1951 | Lundholm |
| 3,208,450 A | 9/1965 | Abelson |
| 3,832,931 A | 9/1974 | Talan |
| 4,278,091 A | 7/1981 | Borzone |
| 4,341,206 A | 7/1982 | Perrett et al. |
| 4,522,202 A | 6/1985 | Otte et al. |

(Continued)

FOREIGN PATENT DOCUMENTS

| EP | 0042657 | 12/1981 |
| EP | 0330328 A1 | 8/1989 |

(Continued)

OTHER PUBLICATIONS

"Bone Mulch Screw Technique" 1996 by Arthrotek, Inc.

(Continued)

Primary Examiner — Kevin T Truong
Assistant Examiner — Michael Araj
(74) Attorney, Agent, or Firm — Harness, Dickey

(57) ABSTRACT

An apparatus and method for fixation of a soft tissue graft. The apparatus may include a member having a first surface and a second surface. Each of the surfaces extend a distance relative to one another. A member is operable to resist movement of the apparatus relative to an anatomical portion. An interference member may be provided to fixedly associate the apparatus with the anatomical structure.

24 Claims, 10 Drawing Sheets

(56) References Cited

U.S. PATENT DOCUMENTS

| | | | |
|---|---|---|---|
| 4,592,346 | A | 6/1986 | Jurgutis |
| 4,605,414 | A | 8/1986 | Czajka |
| 4,744,793 | A | 5/1988 | Parr et al. |
| 4,755,183 | A | 7/1988 | Kenna |
| 4,793,335 | A | 12/1988 | Frey et al. |
| 4,793,355 | A | 12/1988 | Crum et al. |
| 4,828,562 | A | 5/1989 | Kenna |
| 4,950,270 | A | 8/1990 | Bowman et al. |
| 4,960,420 | A | 10/1990 | Goble et al. |
| 4,988,351 | A | 1/1991 | Paulos et al. |
| 5,013,316 | A | 5/1991 | Goble et al. |
| 5,024,669 | A | 6/1991 | Peterson et al. |
| 5,047,032 | A | 9/1991 | Jellicoe |
| 5,047,034 | A | 9/1991 | Sohngen |
| 5,062,843 | A | 11/1991 | Mahony, III |
| 5,108,397 | A | 4/1992 | White |
| 5,108,431 | A | 4/1992 | Mansat et al. |
| 5,112,335 | A | 5/1992 | Laboureau et al. |
| 5,152,765 | A | 10/1992 | Ross et al. |
| 5,211,647 | A | 5/1993 | Schmieding |
| 5,234,434 | A | 8/1993 | Goble et al. |
| 5,282,802 | A | 2/1994 | Mahony, III |
| 5,306,301 | A | 4/1994 | Graf et al. |
| 5,354,300 | A | 10/1994 | Goble et al. |
| 5,356,435 | A | 10/1994 | Thein et al. |
| 5,376,119 | A | 12/1994 | Zimmermann et al. |
| 5,385,567 | A | 1/1995 | Goble |
| 5,393,302 | A | 2/1995 | Clark et al. |
| RE34,871 | E | 3/1995 | McGuire et al. |
| 5,425,767 | A | 6/1995 | Steininger et al. |
| 5,431,651 | A | 7/1995 | Goble |
| 5,454,811 | A | 10/1995 | Huebner |
| 5,456,685 | A | 10/1995 | Huebner |
| 5,507,750 | A | 4/1996 | Goble et al. |
| D374,286 | S | 10/1996 | Goble et al. |
| D374,287 | S | 10/1996 | Goble et al. |
| D374,482 | S | 10/1996 | Goble et al. |
| D375,791 | S * | 11/1996 | Goble et al. ............ D24/145 |
| 5,575,819 | A * | 11/1996 | Amis ................ 623/13.13 |
| 5,628,751 | A | 5/1997 | Sander et al. |
| 5,632,748 | A | 5/1997 | Beck, Jr. et al. |
| 5,645,588 | A | 7/1997 | Graf et al. |
| 5,669,909 | A | 9/1997 | Zdeblick et al. |
| 5,674,224 | A | 10/1997 | Howell et al. |
| 5,741,266 | A | 4/1998 | Moran et al. |
| 5,755,718 | A | 5/1998 | Sklar |
| 5,891,150 | A | 4/1999 | Chan |
| 5,899,938 | A | 5/1999 | Sklar et al. |
| 5,931,869 | A * | 8/1999 | Boucher et al. ............ 128/898 |
| 5,941,883 | A | 8/1999 | Sklar |
| 5,961,520 | A | 10/1999 | Beck, Jr. et al. |
| 6,056,750 | A | 5/2000 | Lob et al. |
| 6,077,267 | A | 6/2000 | Huene |
| 6,132,433 | A | 10/2000 | Whelan |
| 6,231,606 | B1 * | 5/2001 | Graf et al. ............ 606/232 |
| 6,254,605 | B1 | 7/2001 | Howell |
| 6,280,472 | B1 | 8/2001 | Boucher et al. |
| 6,336,940 | B1 * | 1/2002 | Graf et al. ............ 623/13.14 |
| 6,364,886 | B1 | 4/2002 | Sklar |
| 6,371,988 | B1 | 4/2002 | Pafford et al. |
| 6,436,100 | B1 | 8/2002 | Berger |
| 6,482,232 | B1 | 11/2002 | Boucher et al. |
| 6,498,189 | B1 | 12/2002 | Rogelj et al. |
| 6,533,816 | B2 | 3/2003 | Sklar |
| 6,547,778 | B1 | 4/2003 | Sklar et al. |
| 6,554,862 | B2 | 4/2003 | Hays et al. |
| 6,685,709 | B2 * | 2/2004 | Sklar ................ 606/80 |
| 6,699,286 | B2 * | 3/2004 | Sklar ............ 623/13.17 |
| 6,755,840 | B2 | 6/2004 | Boucher et al. |
| 6,767,350 | B1 | 7/2004 | Lob et al. |
| 7,211,111 | B2 | 5/2007 | Boucher et al. |
| 8,221,498 | B2 | 7/2012 | Boucher et al. |
| 2001/0047206 | A1 | 11/2001 | Sklar et al. |
| 2002/0042615 | A1 | 4/2002 | Graf et al. |
| 2003/0009218 | A1 | 1/2003 | Boucher et al. |
| 2012/0016474 | A1 | 1/2012 | Boucher et al. |

FOREIGN PATENT DOCUMENTS

| | | |
|---|---|---|
| EP | 0358372 | 3/1990 |
| EP | 0408416 | 1/1991 |
| EP | 0409364 | 1/1991 |
| EP | 0630613 | 12/1994 |
| EP | 0893109 | 1/1999 |
| FR | 2702646 | 9/1994 |
| WO | WO-98/22047 | 5/1998 |
| WO | WO-00/04834 | 2/2000 |

OTHER PUBLICATIONS

"Intrafix" www.jnjgateway.com/home.jhtml?page=viewContent&contentId=fc0de00100001512 printed Apr. 14, 2004, by Depuy Mitek a Johnson & Johnson Co. (1 page).

"Trauma Systems," 1990, by Biomet, Inc.

European Search Report mailed Jul. 31, 2008 for European application No. EP 04027643.

Innovasive Devices: "Intrafix Technique fo rTibial Fixation of ACL Grafts," copyright 1999, 6 sheets.

* cited by examiner

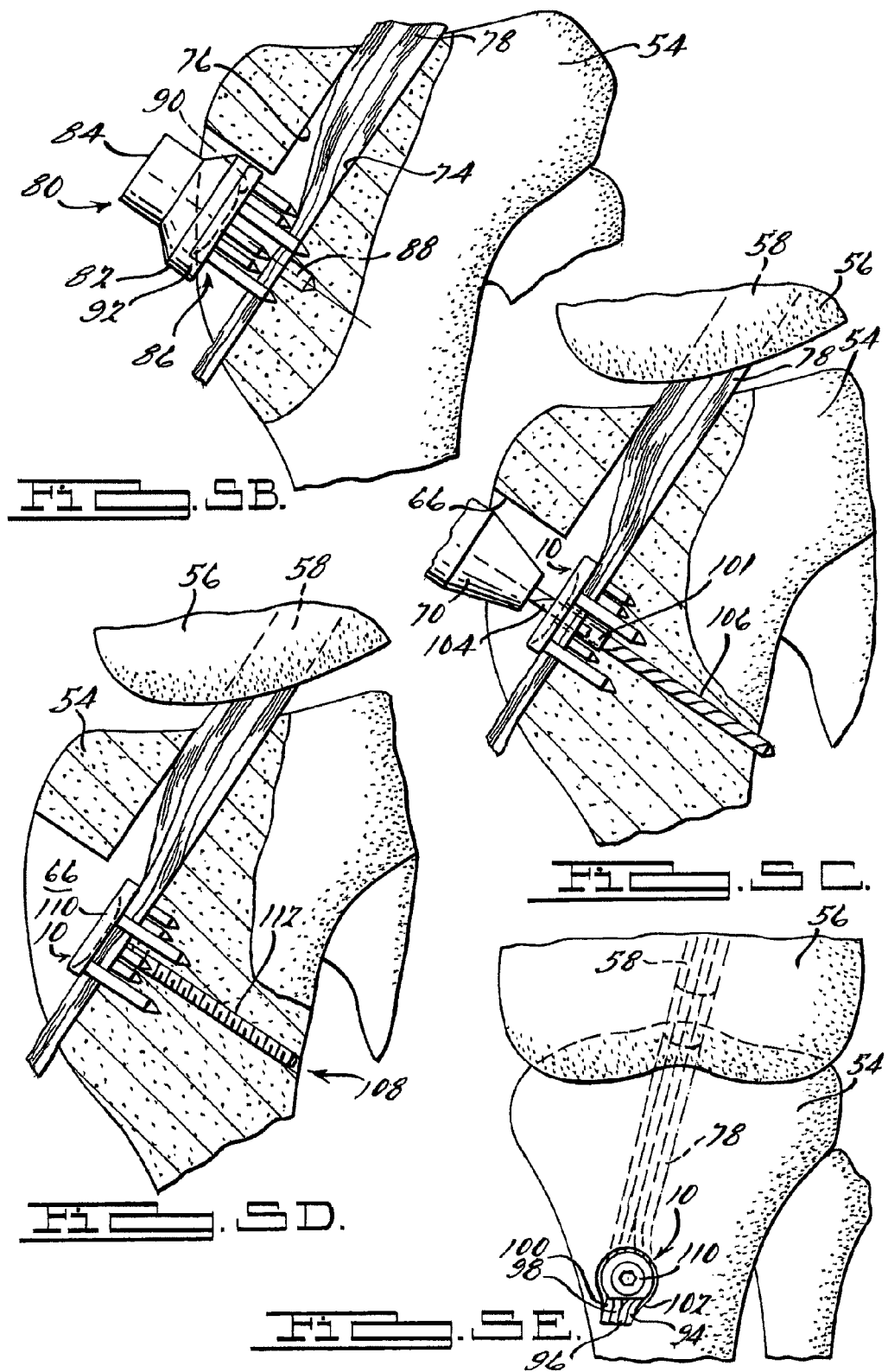

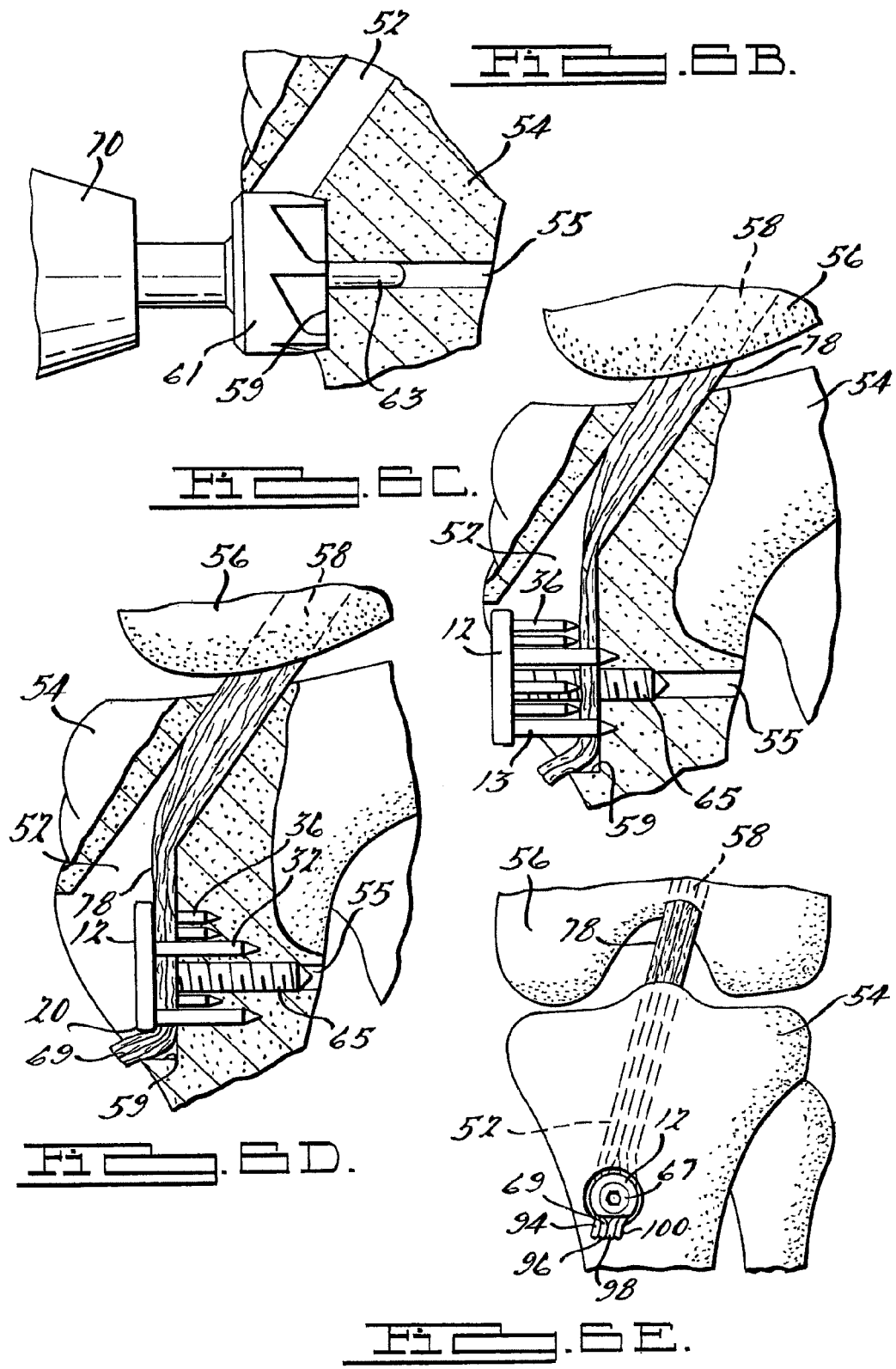

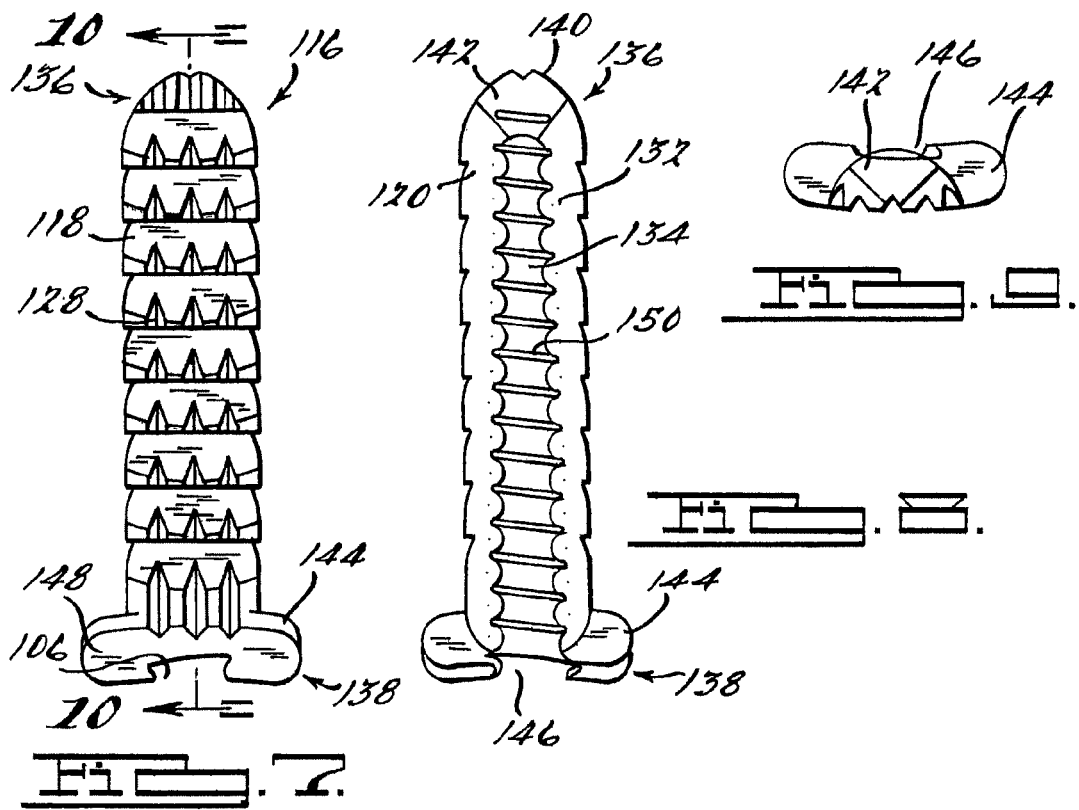
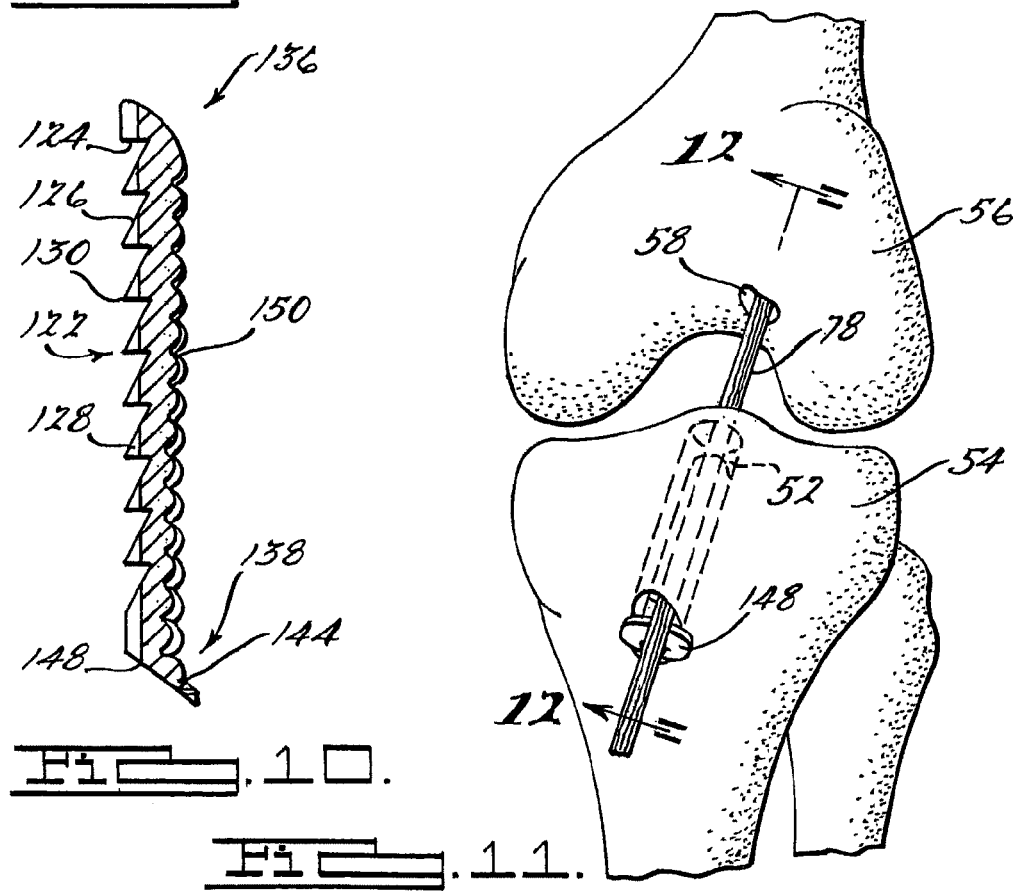

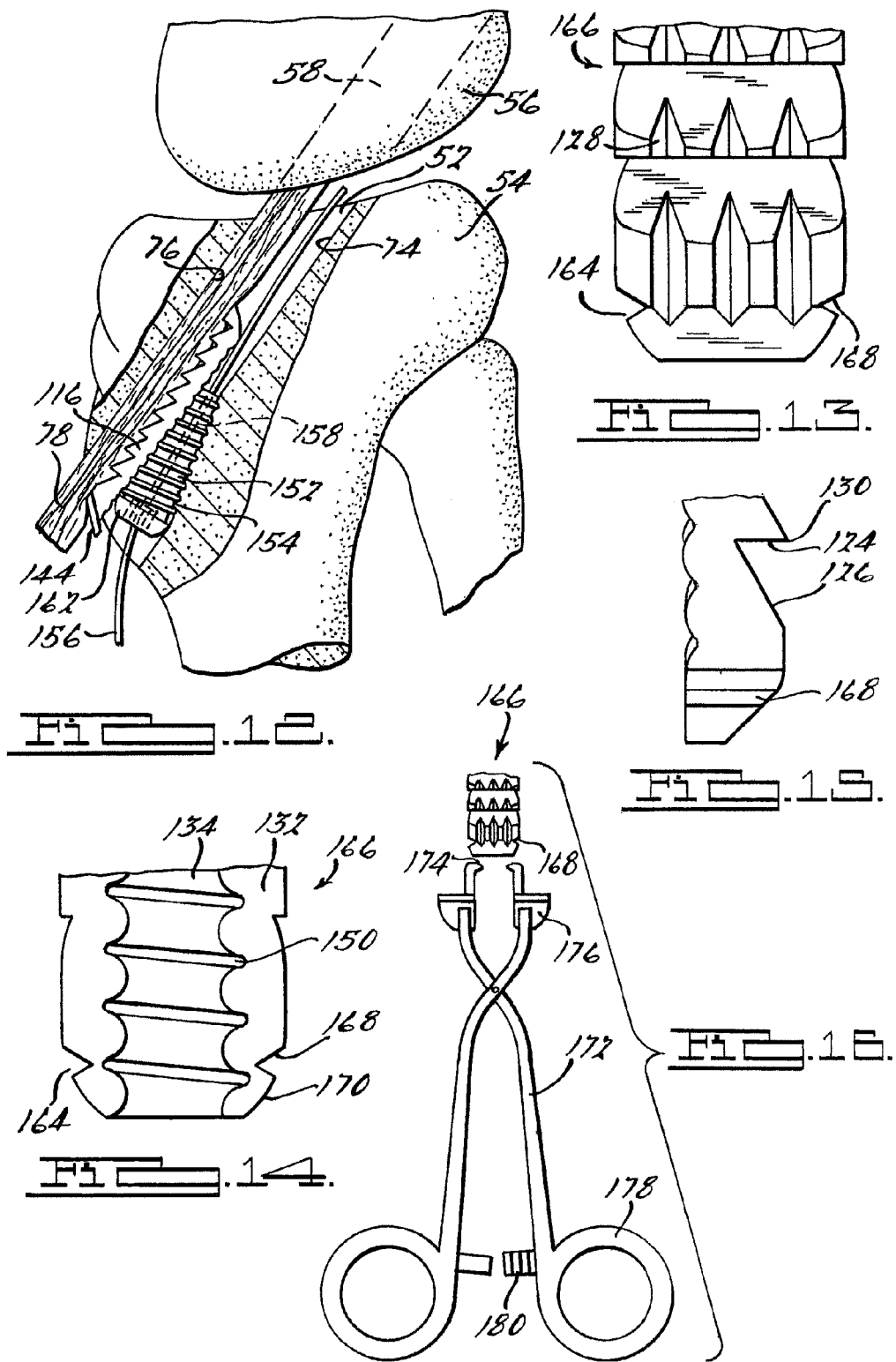

APPARATUS AND METHOD FOR TIBIAL FIXATION OF SOFT TISSUE

CROSS-REFERENCE TO RELATED APPLICATIONS

This application is a divisional of U.S. patent application Ser. No. 11/742,009 filed Apr. 30, 2007, which is a divisional of U.S. patent application Ser. No. 10/874,915 filed Jun. 23, 2004, now U.S. Pat. No. 7,211,111 issued May 1, 2007, which is a divisional of U.S. patent application Ser. No. 10/167,074 filed Jun. 10, 2002, now U.S. Pat. No. 6,755,840 issued Jun. 29, 2004, which is a divisional of U.S. Ser. No. 09/616,544 filed on Jul. 14, 2000, now U.S. Pat. No. 6,482,232 issued Nov. 19, 2002, which is a continuation of U.S. Ser. No. 09/356,959 filed Jul. 19, 1999, now U.S. Pat. No. 6,280,472 issued Aug. 28, 2001, which is a continuation-in-part of U.S. Ser. No. 08/900,602 filed Jul. 23, 1997, now U.S. Pat. No. 5,931,869 issued Aug. 3, 1999. The disclosures of the above applications are incorporated herein by reference.

FIELD OF THE INVENTION

This invention relates generally to an apparatus and method for use in orthopedic surgery and, more particularly, to an apparatus and method for tibial fixation of a soft tissue graft through a tibial bore.

BACKGROUND OF THE INVENTION

Ligaments are strong fibrous connective soft tissue which connect the articular ends of bones to bind them together and to facilitate or limit motion. Injuries to ligaments are common, and patients who are physically active are generally more susceptible to such ligament injuries. The anterior cruciate ligament (ACL) of the knee joint is a ligament frequently injured by such patients. Such injuries cause instability in the knee joint which, when left untreated, may lead to degenerative arthritis. Because of this condition, ACL reconstruction may be required. Generally during ACL reconstruction, a substitute soft tissue ligament or graft is attached to the femur and/or tibia to facilitate regrowth and permanent attachment.

One method of performing this reconstruction involves the use of a section of bone-patellar tendon-bone as a graft. With this method, a ligament tunnel is bored into both the femur and the tibia and the bone-patellar tendon-bone graft is centered between the tunnel. The bone portions of the graft are then each secured within the respective tunnel by tightening an interference screw in each tunnel between the bone graft and the side of the tunnel.

However, use of such a technique presents several disadvantages. For example, the graft may be inadvertently cut or frayed by the sharp edges of the interference screw during insertion of the screw and subsequent to fixation. Moreover, if the interference screw or the bone graft is slightly oversized versus the size of the tunnel, the interference screw may cause too much force to be exerted on the bone graft portion as the interference screw is tightened. This may subsequently cause the bone graft portion to be damaged and not usable. In addition, it is often difficult to accurately gauge the length of the bone-patellar tendon-bone graft in relation to the ligament tunnels such that the bone graft portions may not seat appropriately within the tunnels or be properly tensioned.

Another method for performing this reconstruction involves the use of only a soft tissue ligament graft. Such a graft is generally taken from the hamstring ligament, specifically, the semitendinosus and gracilis ligaments or tendons. Such grafts are generally fed through the ligament tunnel and secured outside the tunnel. The graft is generally secured by a non-endoscopic means of stapling or screwing the graft onto the outside surface of the tibia and/or femur.

However, this method of securing the soft tissue graft also exhibits disadvantages. For example, since the various staple or screw and washer assemblies in existence are positioned on the outside of the bone surface or extend beyond the bone surface, such components are more easily noticed by the patient and in some instances may cause patient discomfort. In addition, because of the discomfort, it may be required to perform subsequent surgery to remove the staple or screw and washer assembly once the graft has permanently attached to the bone, thereby subjecting the patient to a second surgery, as well as increasing overall surgical costs. The staple or screw and washer assembly are also not substantially resistant to slippage and do not provide stiff securement. In other words, the graft may permanently slip under the securement of the staple or screw and washer assembly thereby providing a non-optimum tension on the graft. Securement at the anchoring point may be resilient such that if the graft utilizes sutures in combination with the staple or screw washer assembly, the anchoring point may stretch under stress and resiliently return, thereby also providing non-optimum tensioning or stiffness for the graft.

Another method for securing the soft tissue ligament graft within a femoral tunnel is set forth in U.S. Pat. No. 5,431,651. This reference uses a cleated washer which engages the soft tissue graft within the femoral tunnel by use of a transverse cannulated set screw. The cleated washer is drawn into the femoral tunnel by use of a suture coupled to the washer and pulled through the cannulated set screw. Once in position adjacent to the set screw, the set screw engages the cleated washer against the soft tissue ligament and the wall of the tunnel.

However, this method of securing a soft tissue graft within a femoral tunnel also exhibits many disadvantages. For example, such a procedure will generally require more surgical time since it includes the added steps of passing a suture through a cannulated set screw and down the femoral tunnel, as well as attaching it to the cleated washer itself. This also makes it extremely difficult to properly align the cleated washer since the cleated washer must be pulled through and aligned using a flexible non-rigid suture. Additionally, it may be difficult to maintain the location of the cleated washer as the set screw is engaged against the washer since the suture does not rigidly hold or maintain the position of the cleated washer. Finally, by drawing the cleated washer up through the femoral tunnel, a larger femoral tunnel may be required and the spikes on the cleated washer may cut or fray the soft tissue graft as it is passed through the femoral tunnel.

What is needed then is an apparatus and method for tibial fixation of a soft tissue graft which does not suffer from the above-identified disadvantages. This in turn, will reduce the possibility for damaging the soft tissue graft; reduce the possibility for requiring a new graft from being harvested; provide for endoscopic securement of a soft tissue graft without damaging the graft; reduce or eliminate potential patient discomfort; provide endoscopic fixation which is flush to the bone surface; reduce or eliminate the need for a subsequent surgery to remove fixation components after the graft has been permanently attached to the bone; provide increased fixation strength; provide less pretensioning of the graft to restore knee stability, thereby not over-constraining the knee after setting the tension on the graft; reduce or eliminate the potential for slippage of the soft tissue graft; increase stiffness and mechanical behavior of the soft tissue graft; reduce the number of steps to secure the soft tissue graft; and reduce the number of separate instrumentation required to secure the soft tissue grafts. It is, therefore, an object of the present invention to provide such an apparatus and method for tibial fixation of a soft tissue graft.

SUMMARY OF THE INVENTION

In accordance with the teachings of the present invention, an apparatus and method for tibial fixation of a soft tissue graft is disclosed. The apparatus and method flushly secures the soft tissue graft within a tunnel formed in the tibia. This is basically achieved by utilizing an apparatus which does not extend beyond the tibia upon securing the graft within a tibial tunnel.

In one preferred embodiment, an apparatus for fixation of a soft tissue graft includes a body having a first side and a second side. A first plurality of spikes extend from the second side of the body each having a first length. A second plurality of spikes extend from the second side of the body each having a second length. The first length is longer than the second length such that the first plurality of spikes are operable to engage the bone without the second plurality of spikes substantially engaging the soft tissue graft to permit proper tensioning of the soft tissue graft.

In another preferred embodiment, an apparatus for fixation of a soft tissue graft within a counterbore formed into the bone includes a body having a first and second side. The body includes a substantially cylindrical sidewall and a substantially planar relief formed into a portion of the cylindrical sidewall. A plurality of spikes extend from the second side of the body and are operable to engage the bone. The substantially planar relief is operable to permit the body to be flushly received within the counterbore and permit the soft tissue graft to exit the counterbore without substantially binding on the cylindrical sidewall and the counterbore.

In another preferred embodiment, an apparatus for fixation of a soft tissue graft within a tunnel formed in a bone includes a wedge having a first side and a second side. The first side includes a plurality of teeth which are operable to engage the soft tissue graft against the tunnel. The second side includes a threaded face operable to axially receive an interference screw. Means are provided for preventing the wedge from axially extending into the tunnel more than a predetermined amount.

In another preferred embodiment, a method for fixation of a soft tissue graft includes forming a tunnel in a bone having an entrance opening. Forming a counterbore substantially perpendicular with the tunnel and partially within the entrance opening. Passing a soft tissue graft through the tunnel along the counterbore. Securing the soft tissue graft within the counterbore with an apparatus which is nested within the counterbore.

In another preferred embodiment, a method for fixation of a soft tissue graft includes forming a tunnel in a bone. Forming a pilot hole adjacent to an entrance opening of the tunnel. Forming a counterbore substantially concentric with the pilot hole and partially within the entrance opening. Passing a soft tissue graft through the tunnel along the counterbore. Securing the soft tissue graft within the counterbore with an apparatus which is flushly received within the counterbore.

In yet another preferred embodiment, a method for fixation of a soft tissue graft in a bone includes forming a tunnel in the bone. Forming a guide bore substantially perpendicular to the tunnel. Forming a counterbore substantially perpendicular to the tunnel by use of the guide bore. Passing a graft into the tunnel and along the counterbore and securing the graft within the counterbore.

In another preferred embodiment, a method for fixation of a soft tissue graft in a bone with a fixation apparatus includes forming a tunnel in the bone. Forming a counterbore extending into the tunnel. Providing a combination implant and guide instrument. Passing the graft into the tunnel and along the counterbore. Implanting the fixation apparatus within the counterbore by use of a combination implant and guide instrument to secure the graft within the tunnel. Guiding a drill bit with the combination implant and guide instrument to form a bore relative to the tunnel. Passing a fixation screw through the fixation apparatus and into the bore to firmly secure the graft within the tunnel.

In a further preferred embodiment, a method for fixation of a soft tissue graft in a bone includes forming a tunnel in the bone. Slidably inserting a counterbore guide into the tunnel having a guide bushing substantially perpendicular to the tunnel. Forming a guide bore substantially perpendicular to the tunnel by use of the guide bushing. Forming a counterbore substantially perpendicular to the tunnel by use of the guide bore. Passing the graft into the tunnel and along the counterbore and securing the graft within the counterbore.

According to various embodiments an apparatus to assist in fixing a member relative to an anatomy is disclosed. The apparatus may include a first member including a first portion and a second portion. An interference member may selectively associate the first member with the anatomy. An interference portion associated with the first member may assist holding the first member at a selected position relative to the anatomy. The interference member is operable to be associated with the first member at a selected time.

According to various embodiments an apparatus to assist in fixing a member relative to an anatomy may include the apparatus extending between a first end and a second end including a first wall and a second wall. A portion of a thread may be defined by the first wall and an engaging surface may be defined by the second wall. An interference member may be operable to interact with the thread to assist in holding the apparatus in a selected position relative to the anatomy.

According to various embodiments a method of using an apparatus, including a first side and a second side, to assist in fixing a member relative to an anatomy is disclosed. The method may include forming a bore in the anatomy. The apparatus may be positioned relative to the bore. A graft may be engaged with the apparatus. An interference member may associate the apparatus with the anatomy relative to the bore defined by the anatomy. Also the apparatus may be held in a selected position relative to the anatomy in the bore.

According to various embodiments an apparatus kit for positing a soft tissue graft relative to a portion of the anatomy is disclosed. The apparatus kit may includes a first member including an interference portion and an engaging portion. Also, an interference member may be provided with the apparatus kit. A holding apparatus associable with the first member may assist holding the first member at a selected position relative to the anatomy.

BRIEF DESCRIPTION OF THE DRAWINGS

Still other advantages of the present invention will become apparent to those skilled in the art after reading the following specification by reference to the drawings in which:

FIGS. 5A-5E illustrates a method for attaching a soft tissue graft using the tibial fixation apparatus according to the teachings of the present invention;

FIG. 6A-6E illustrates another method for attaching a soft tissue graft using the tibial fixation apparatus according to the teachings of the present invention;

FIG. 7 is a top view of another apparatus for tibial fixation of a soft tissue graft according to the teachings of the present invention;

FIG. 8 is a bottom view of the tibial fixation apparatus of FIG. 7;

FIG. 9 is a front view of the tibial fixation apparatus of FIG. 7;

FIG. 10 is a side cross-sectional view of the tibial fixation apparatus of FIG. 7 taken along line 10-10 of FIG. 7;

FIG. 11 is a perspective view illustrating a method for positioning the tibial fixation apparatus of FIG. 7;

FIG. 12 is a side cross-sectional view taken along line 12-12 of FIG. 11 illustrating the method for positioning the tibial fixation apparatus of FIG. 7;

FIG. 13 is a top-end view of another apparatus for tibial fixation of a soft tissue graft according to the teachings of the present invention;

FIG. 14 is a bottom-end view of a tibial fixation apparatus of FIG. 13;

FIG. 15 is a side-end view of the tibial fixation apparatus of FIG. 13;

FIG. 16 is a top view of an instrument utilized for grasping the tibial fixation apparatus of FIG. 13;

DETAILED DESCRIPTION OF VARIOUS EMBODIMENTS

The following description of various embodiments concerning an apparatus and method for tibial fixation of soft tissue grafts are merely exemplary in nature and are in no way intended to limit the invention or its application or uses. Moreover, while the present invention is described in detail below with reference to tibial fixation of soft tissue grafts through a tibial tunnel, it will be appreciated by those skilled in the art that the present invention is clearly not limited to fixation in a tibial tunnel and may be utilized to secure soft tissue grafts, tendons, ligaments, etc. in various other tunnels, bores or adjacent to a bone.

Figure 1:
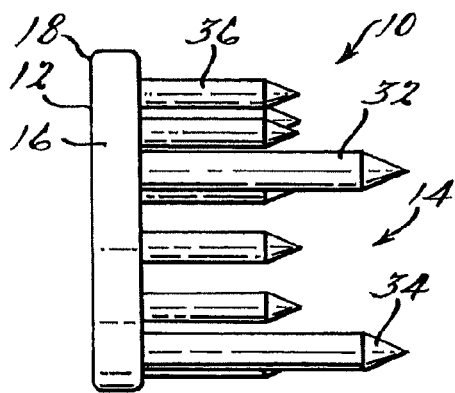
FIG. 1 is a side view of an apparatus for tibial fixation of a soft tissue graft according to the teachings of the present invention.
Figure 2:
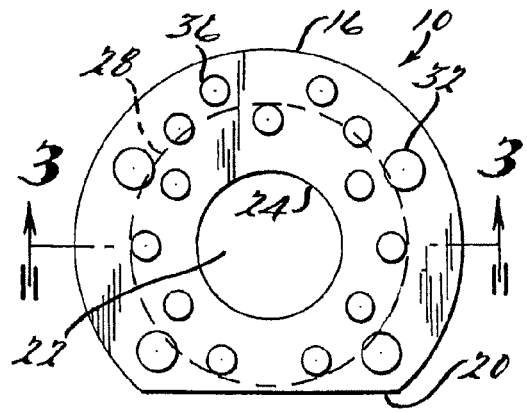
FIG. 2 is a top view of the tibial fixation apparatus of FIG. 1.
Figure 3:
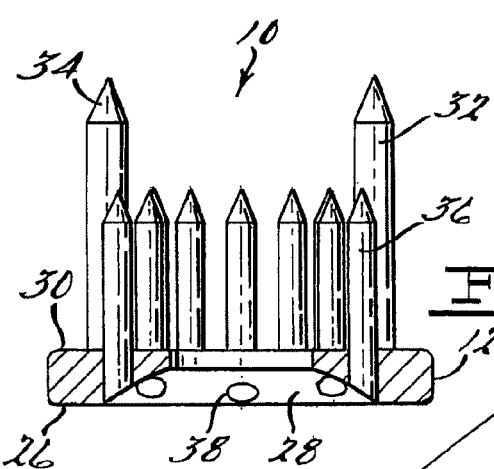
FIG. 3 is a side cross-sectional view of the tibial fixation apparatus of FIG. 1 taken along line 3-3 of FIG. 2.

Referring to FIGS. 1-3, an apparatus 10 for tibial fixation of a soft tissue graft according to the teachings of one embodiment of the present invention is shown. The apparatus or washer 10 includes a cylindrical body 12 having a diameter of about 16 millimeters and a plurality of spikes 14. The cylindrical body 12 includes a substantially cylindrical sidewall 16 having beveled or rounded edges 18 and a substantially flat planar relief face 20 formed into a portion of the cylindrical sidewall 16. The body 12 further defines a concentric internal bore 22 having an internal sidewall 24 with a diameter of about 0.234 inches which is adapted to receive a compression bone screw, further discussed herein. A first side or top 26 of the body 12 includes a concentric counterbore 28 operable to flushly receive a head of the compression screw. A second side or bottom 30 of the body 12 is substantially planar and has the plurality of spikes 14 extending out from the second side 30.

The plurality of spikes 14 includes a first plurality or four cylindrical guide spikes 32 each having a length from the top 26 of the body 12 to the tip 34 of the spikes 32 of about 0.52 inches and a cylindrical diameter of about 0.062 inches. The four spikes 32 are positioned concentrically about the body 12 at a radius of about 0.25 inches from the center of the body 12. The plurality of spikes 14 further includes a second plurality or thirteen cylindrical engagement spikes 36 each having a length from the top 26 of the body 12 to the tip 34 of the spikes 36 of about 0.34 inches and a cylindrical diameter of about 0.047 inches. The cylindrical spikes 32 and 36 each include the pointed end 34 operable to engage and penetrate cancellous and cortical bone. The engagement spikes 36 are positioned between the guide spikes 32 and the internal bore 22 in such a manner that the engagement spikes 36 are able to penetrate and secure the soft tissue graft at multiple sites, further discussed herein.

The apparatus or washer 10 is preferably made from a suitable biocompatible material such as titanium, stainless steel, titanium alloy, cobalt-chrome-molybdenum alloy, polymer, resorbable polymer, etc. The apparatus 10 preferably consists of an assembly of separate spikes 14 which are welded to the body 12, via welds 38. Alternatively, the apparatus 10 may be cast or machined to the required shape and size.

Figure 4:
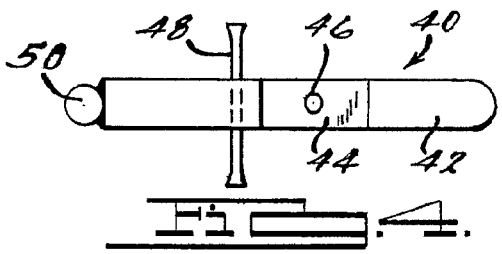
FIG. 4 is a top view of a counterbore drill guide used in preparing a counterbore to nestingly receive the tibial fixation apparatus of FIG. 1.
Figure 5A:
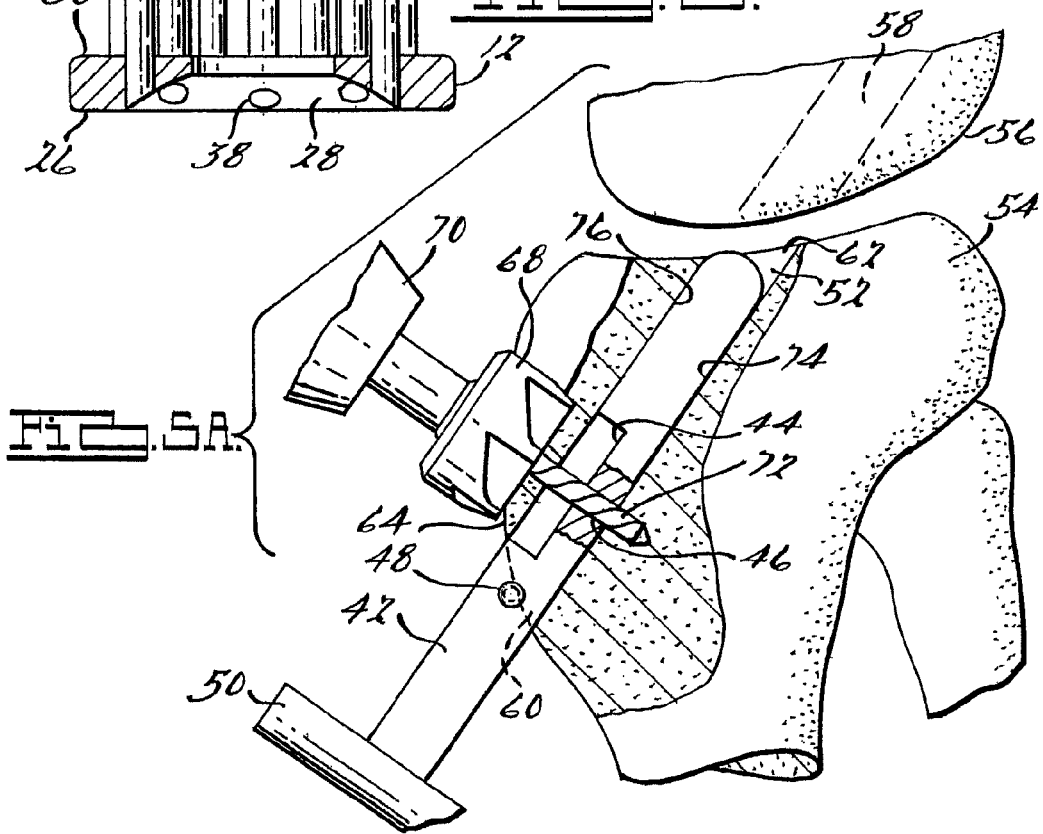
Figure 6A:
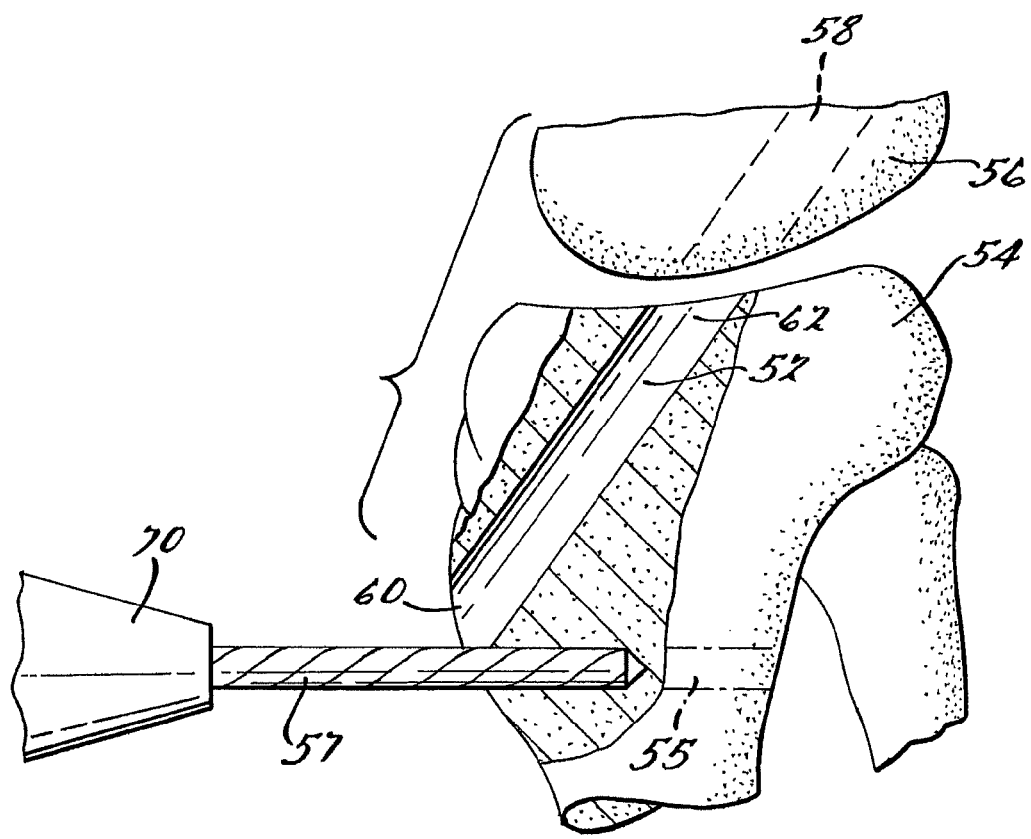

Referring to FIG. 4, a counterbore drill guide 40 is shown for use in preparation of a substantially perpendicular counterbore relative to a tibial tunnel formed in a tibia, further discussed herein. The counterbore drill guide 40 includes a substantially cylindrical body 42 defining a planar notched region 44 having a center aperture 46 for receipt of a counterbore drill bit. Positioned adjacent to the notched region 44 is a positioning bar 48 passing medially through the body 42. The positioning bar 48 is slidably engaged with the body 42 and is utilized to engage the medial cortex of the tibia to provide a predetermined insertion length of the counterbore drill guide 40 into the tibial tunnel. Set back from the positioning bar 48 is a T-shaped handle 50 which can be utilized by the surgeon to hold the counterbore drill guide 40 during counterbore drilling. The body 42 of the counterbore drill guide 40 is about 7 millimeters in diameter, with the notched region 44 beginning at about 20 millimeters from a distal end of the drill guide 40. The notched region 44 is about 17 millimeters wide having about a 3.5 millimeter diameter centering hole 46. The positioning bar 48 is set back about 10 millimeters from the center of the centering hole 46, thereby providing a predetermined insertion length within the tibial tunnel of about 38.5 millimeters. The counterbore drill guide 40 is preferably made from stainless steel or other suitable material.

Turning to FIGS. 5A-5E, one method for tibial fixation of a soft tissue graft will now be described. Initially, soft tissue grafts are harvested for use in an anterior cruciate ligament (ACL) reconstruction. The semitendinosus and gracilis tendons from their respective hamstring muscles are generally used and harvested from the patient or by way of donor tendons using techniques well known in the art. Alternatively, synthetic grafts may also be employed. The harvested grafts will generally consist of two tubular grafts which are subsequently looped at their mid-section to form a four bundle graft. The four bundle graft should be sized to pass without friction through a tibial and femoral tunnel.

Once the grafts have been harvested and prepared using known techniques, tunnel or hole placement is then performed. A tibial tunnel or bore 52 is drilled through the tibia 54 and into the femur 56 creating a femoral tunnel 58. The tibial tunnel 52 will typically have a diameter between about 7 to 13 millimeters, preferably 8-9 millimeters, and is bored utilizing a drill bit and a driver. The tibial tunnel 52 exits at about the center of the tibial plateau and enters the tibia 54 at about 50 millimeters from the top of the tibial plateau medial to the tibial tubercle or at the medial cortex. Since the tibial tunnel 52 angles through the tibia 54, it creates an elliptical entrance opening 60 and an elliptical exit opening 62. The drill bit utilized to bore the tibial tunnel 52 also generally bores the femoral tunnel 58 in the femur 56 by continuing to extend the drill bit through the tibial tunnel 52 and into the femur 56. The tibial tunnel 52 and the femoral tunnel 58 are bored using techniques well known in the art which may include the use of alignment or drill guide mechanisms in combination with a drill bit and driver.

Once the tibial tunnel 52 is bored through the tibia 54, the body 42 of the counterbore drill guide 40 is axially slid into the entrance opening 60 of the tibial tunnel 52. The counterbore drill guide 40 is advanced into the tibial tunnel 52 until the positioning bar 48 is flush against the medial cortex of the tibia 54. This will align the centering hole 46 adjacent to an anterior edge 64 of the entrance opening 60 of the tibial tunnel 52.

With the counterbore drill guide 40 properly positioned within the tibial tunnel 52 and held by the handle 50, a counterbore 66 is formed substantially perpendicular to the tibial tunnel 52 using a counterbore bit 68 and a drive mechanism 70. The counterbore bit 68 includes a centering nose 72 which rotatably engages the centering hole 46 formed into the counterbore drill guide 40. The centering nose 72 is formed similar to a drill bit so that the centering nose 72 drills into the tibia 54. The counterbore 66 is preferably bored to remove the anterior edge 64 of the entrance opening 60 providing a substantially perpendicular counterbore 66. In other words, the centering nose 72 is directed through the tibia 54 and inserted in the centering hole 46 in the counterbore drill guide 40 such that the counterbore bit 68 is perpendicular to a posterior wall 74 of the tibial tunnel 52. The counterbore bit 68 is advanced to remove the anterior tibial cortex adjacent to an anterior wall 76 until it seats in the notch region 44 in the counterbore drill guide 40. The bone reamings may then be collected and saved for subsequent grafting of the tibial tunnel 52.

Once the counterbore 66 has been formed utilizing the counterbore bit 68, a four bundle graft 78 is first secured within the femoral tunnel 58 of the femur 56 using one of many techniques known in the art. Preferably, the four bundle graft 78 is secured within the femoral tunnel 58 of the femur 56 by means of a bone mulch screw, set forth in U.S. Pat. No. 5,674,224, "BONE MULCH SCREW ASSEMBLY FOR ENDOSTEAL FIXATION OF SOFT TISSUE GRAFTS AND METHOD FOR USING SAME", which is hereby incorporated by reference. With the graft 78 secured within the femoral tunnel 58, the graft 78 extends out through the tibial tunnel 52.

The apparatus 10 is then engaged and secured to the tibia 54 by use of an impactor 80 in combination with a mallet. The impactor 80 has a generally cylindrical body 82 which tapers to a striking end 84. The impactor 80 includes a complimentary face 86 having a concentric guide post 88 which is received within the internal bore 22 and an arcuate surface 90 which is received within the counterbore 28. The impactor 80 further includes an edge guide 92 which engages and mates with the planar relief face 20 formed within the apparatus 10. The edge guide 92 enables the surgeon to properly rotatably align the apparatus 10 by simply rotating the impactor 80 within the counterbore 66 and engaging the planar face 20 with the edge guide 92.

The graft 78 is oriented such that two grafts 94 and 96 of the four bundle graft 78 pass along a first side of the guide post 88 and two grafts 98 and 100 pass along a second side the guide post 88 such that each pair of grafts are positioned or guided between the guide post 88 and the longer guide spikes 32. The apparatus 10 is initially partially engaged with only the guide spikes 32 penetrating cancellous and cortical bone of the tibia 54 and the relief face 20 directed toward the entrance opening 60. With the guide spikes 32 engaging the tibia 54, the four bundle graft 78 is appropriately tensioned by pulling the four bundle graft 78 under the engagement spikes 36 within the counterbore 66 and out of an area 102 defined by the relief 20 and the counterbore 66 without binding on the sidewall 16 or the counterbore 66. The two stage spikes 14 having the first plurality of spikes 32 of a first length and the second plurality of spikes 36 having a second shorter length enables the apparatus 10 to be initially secured to the tibia 54 with only the spikes 32, while allowing proper tensioning and guiding of the four bundle graft 78.

The four bundle graft 78 is properly tensioned generally by means of pulling on the ends of the graft 78 extending out of the area 102 under the relief 20 manually or with a tensioning device with the knee in full extension. A preferred tensioning device is set forth in U.S. Pat. No. 5,507,750 entitled, "METHOD AND APPARATUS FOR TENSIONING GRAFTS AND LIGAMENTS", which is hereby incorporated by reference. Once the proper tension is achieved, the apparatus 10 is fully seated or nested within the counterbore 66 by use of the impactor 80 and a mallet, as shown clearly in FIG. 5C. Upon seating the apparatus 10, the engagement spikes 36 penetrate the two grafts 94 and 96 on the first side of the guide post 88 at multiple sites and the two grafts 98 and 100 on the second side of the guide post 88 to maintain proper tensioning of the four bundle graft 78. The apparatus or washer 10 thus seats or nests flush within the counterbore 66 thereby eliminating any objects extending out beyond the tibia 54. The relief 20 is also used to eliminate any portion of the apparatus 10 from extending out beyond the tibia 54.

With the apparatus 10 fully nested within the counterbore 66 or posterior wall 74 of the tibia tunnel 52, a drill guide 101 is inserted into the internal bore 22 of the apparatus 10 to maintain the separation of the four bundle graft 78. The drill guide 101 is advanced between the two grafts 94 and 96 on the first side of the guide post 88 and the two grafts 98 and 100 on the second side of the guide post 88 so that it is flush against the posterior wall 74 of the tibial tunnel 52. A 3.5 millimeter drill bit 104 attached to the driver 70 is then utilized to drill a bore 106 through the tibia 54 to the posterior cortex of the tibia 54. Once the bore 106 is drilled through the tibia 54, the depth of the bore 106 is measured and the posterior cortex region is tapped using an appropriate tap.

With the bore 106 formed and tapped, a low profile compression screw 108 is inserted into the internal bore 22 and screwed into the bore 106 in the tibia 54 to threadably secure the compression screw 108 within the bore 106 and complete the fixation of the apparatus 10 within the counterbore 66. The compression screw 108 includes a head 110 which is flushly received within the counterbore 28, a threaded section 112, and a cylindrical non-threaded section 114 passing through the body 12 of the apparatus 10. Once the compression screw 108 has been fully secured, the ends of the grafts 94-100 may be trimmed back within the area 102. The apparatus 10 provides a substantially stiff and slippage free anchoring for the graft 78.

Turning to FIGS. 6A-6E, another method for tibial fixation of a soft tissue graft will now be described. In this regard, like reference numerals will be used to reference to like structures. Once the grafts have been harvested and prepared using the known techniques, tunnel or hole placement is again performed. The tibial tunnel or bore 52 is drilled through the tibia 54 and into the femur 56 creating a femoral tunnel 58. The tibial tunnel 52 will typically have a diameter between about 7 to 13 millimeters, preferably 8-9 millimeters, and is bored utilizing a drill bit and a driver. The tibial tunnel 52 exits at about the center of the tibial plateau and enters the tibia 54 at about 50 millimeters from the top of the tibial plateau medial to the tibial tubercle or at the medial cortex. Since the tibial tunnel 52 angles through the tibia 54, it creates an elliptical entrance opening 60 and an elliptical exit opening 62. The drill bit utilized to bore the tibial tunnel 52 also generally bores the femoral tunnel 58 in the femur 56 by continuing to extend the drill bit through the tibial tunnel 52 and into the femur 56. The tibial tunnel 52 and the femoral tunnel 58 are bored using techniques well known in the art which may include the use of alignment or drill guide mechanisms in combination with a drill bit and driver.

Once the tibial tunnel 52 is bored through the tibia 54, a pilot hole 55 is bored straight through the tibia 54 parallel with the tibia plateau. Specifically, the pilot hole 55 is started at the intersection point at the bottom of the entrance 60 and is drilled from the anterior medial to posterior lateral side utilizing a drill bit 57 driven by the drive mechanism 70. The pilot hole 55 is preferably about 2 to 3 millimeters in diameter.

Once the pilot hole 55 has been formed or bored, a counterbore 59 is formed at the anterior medial side of the tibia 54 using a counterbore bit 61 and the drive mechanism 70. The counterbore bit 61 includes a pilot nose 63 which engages the pilot hole 55 to accurately align the counterbore bit 61 concentric with the pilot hole 55 and relative to the entrance opening 60. The counterbore 59 is preferably bored to a depth of about 6 to 7 millimeters which intersects with the tibial tunnel 52 or entrance opening 60.

Once the counterbore 59 has been formed utilizing the counterbore bit 61, the four bundle graft 78 is first secured within the femoral tunnel 58 of the femur 56 using one of the many techniques known in the art. Here again, the four bundle graft 78 is preferably secured within the femoral tunnel 58 of the femur 56 by means of the bone mulch screw, set forth in U.S. Pat. No. 5,674,224 "BONE MULCH SCREW ASSEMBLY FOR ENDOSTEAL FIXATION OF SOFT TISSUE GRAFTS AND METHOD FOR USING SAME", which is hereby incorporated by reference. With the graft 78 secured within the femoral tunnel 58, the graft 78 extends out through the tibial tunnel 52.

The apparatus 10 is then engaged to the tibia 54 by means of a bone screw 65 having a head 67 and the spikes 32. The graft 78 is oriented such that the two grafts 94 and 96 of the four bundle graft 78 pass along a first side of the bone screw 65 and two grafts 98 and 100 pass along a second side the bone screw 65 such that the pair of grafts are positioned or guided between the bone screw 65 and the longer guide spikes 32. The apparatus 10 is initially partially engaged with only the guide spikes 32 penetrating cancellous and cortical bone of the tibia 54 and the bone screw 65 partially set.

With the guide spikes 32 engaging the tibia 54, the four bundle graft 78 is appropriately tensioned by pulling the four bundle graft 78 under the engagement spikes 32 along the counterbore 59 and out of an area 69 defined by the relief 20 and the counterbore 59 without binding on the sidewall 16 or the counterbore 59. The two stage spikes 14 having the first plurality of spikes 32 of a first length and the second plurality of spikes 36 having a second shorter length enables the apparatus 10 to be initially secured to the tibia 54 with only the spike 32 and bone screw 65, while allowing tensioning and guiding of the four bundle graft 78.

With the four bundle graft 78 properly tensioned, generally by means of pulling on the ends of the graft 78 extending out of the area 69 under the relief 20, the bone screw 65 is further turned to fully seat the apparatus or washer 10 flush within the counterbore 59, as shown clearly in FIG. 6D. Upon turning the bone screw 65, the engagement spikes 36 penetrate the two grafts 94 and 96 on the first side of the bone screw 65 and the two grafts 98 and 100 on the second side of the bone screw 65 to maintain proper tensioning of the four bundle graft 78. the apparatus or washer 10 thus seats flush within the counterbore 59, thereby eliminating any objects extending out beyond the tibia 54. Once the bone screw 65 has been fully secured, the ends of the grafts 94-100 may be trimmed back within the area 64.

Turning to FIGS. 7-10, an apparatus or wedge 116 for tibial fixation of a soft tissue graft according to the teachings of another embodiment of the present invention is shown. In this regard, like reference numerals will be used to refer like structures. Here again, the wedge 116 is preferably made from a suitable biocompatible material such as titanium, stainless steel, titanium alloy, cobalt-chrome-molybdenum alloy, polymer, resorbable polymer, etc.

The wedge 116 includes a first side 118 and a second side 120. The first side includes a plurality of parallel running teeth 122 each defined by a first vertical sidewall 124 and a second angled sidewall 126. Each tooth 122 includes three axial or perpendicular notches 128 formed into the tooth 122 and an edge 130. The notches 128 being perpendicular to the teeth 122 provides additional surface area, as well as two opposed planes in which to grab or engage the four bundle graft 78. The edge 130 of each tooth 122 has a slight arcuate shape, as shown clearly in FIG. 9. The second side 120 of the wedge 116 includes an arcuate shaped periphery 132 with a threaded face 134 formed therein. The threaded face 134 is operable to be threadably engaged by an interference screw, further discussed herein.

The wedge 116 further includes a first or distal end 136 and a second or proximal end 138. The distal end 136 includes a rounded nose 140 having the three notches 128 on the first side 118 and a V-shaped notch or groove 142 on the second side 120. The proximal end 138 includes a pair of wings 144 defining an open region 146 which provides for clearance of the interference screw. The wings 144 are angled and sized such that when the wedge 116 is axially inserted into the tibial tunnel 52, a face 148 of the wings 144 lies substantially flush or along the same plane as the tibia 54. The size of the wings 144 are also larger than the diameter of the tibial tunnel 52 such that the wings 144 prevent the wedge 116 from being axially inserted or drawn into the tibial tunnel 52 more than a predetermined amount.

Turning to FIG. 10, a side cross-sectional view of the wedge 116 is shown having a wider or thicker distal end 136 and a thinner or narrower proximal end 138. The threaded face 134 is also clearly shown having individual threads 150 formed within the arcuate periphery 132. The orientation of the thinner proximal end 138 which gets thicker moving out to the distal end 136 compensates or is complimentary to the shape of the interference screw utilized. This sizing also provides engagement adjustment by locating the interference screw either further in along the threaded face 134 near the distal end 136 or conversely locating the interference screw back towards the proximal end 138, further discussed herein.

Referring to FIGS. 11-12, the method for tibial fixation of the soft tissue graft 78 utilizing the wedge 116 will now be described. Here again, the soft tissue grafts are initially harvested and prepared for use in the anterior cruciate ligament (ACL) reconstruction. Once the grafts have been harvested and prepared using known techniques, the tibial tunnel 52 is bored through the tibia 54 and into the femur 56 creating the femoral tunnel 58. The four bundle graft 78 is then secured within the femoral tunnel 58 using the bone mulch screw described above. Once the four bundle graft 78 has been secured within the femoral tunnel 58, the four bundle graft 78 is passed through the tibial tunnel 52.

With the four bundle graft 78 extending out of the tibial tunnel 52, the four bundle graft 78 is properly tensioned by pulling on the proximal end of the four bundle graft 78. With the four bundle graft 78 properly tensioned, the wedge 116 is positioned axially in the tibial tunnel 52 below the four bundle graft 78. The first side 118 having the plurality of teeth 122 are oriented axially and adjacent to the four bundle graft 78 to substantially engage and hold the four bundle graft 78 under proper tensioning against the upper or anterior side 76 of the tunnel 52. An interference screw 152 having threads 154 which matingly receive threaded face 134 is axially inserted within the tibial tunnel 52. An optional guide wire 156 may be utilized which passes through a bore 158. The guide wire 156 passes from the entrance opening 60 out the exit opening 62 and is used for positioning and aligning the interference screw 152 during axial insertion of the interference screw 152.

With the interference screw 152 properly positioned between the second side 120 of the wedge 116 and the lower or posterior sidewall 74 of the tibial tunnel 52, a driver, such as a hex driver engages the head 162 of the interference screw 152 to axially drive the interference screw 152 between the second side 120 and the sidewall 74. As the driver turns the interference screw 152, the threads 154 of the interference screw 152 engage the threads 150 of the threaded face 134, as well as the sidewall 74, thereby causing the interference screw 152 to axially advance from the proximal end of the tunnel 52 to the distal end of the tunnel 52. As the interference screw 152 axially advances, the wings 144 prevent the wedge 116 from being axially drawn into the tibial tunnel 52 by more than a predetermined amount, as well as maintains the pre-set tension on the four bundle graft 78. As the interference screw 152 further ascends into the tibial tunnel 52, the teeth 122 further engage and compress the four bundle graft 78 under the wedge compression of the interference screw 152. The side cross-section wedge shape of the wedge 116, as shown in FIG. 10, is complimentary to the shape of the interference screw 152, such that initial engagement of the interference screw 152 with the wedge 116 provides a substantially planer uniform force which is substantially transverse or perpendicular to the tibial tunnel 52. Upon further driving the interference screw 152 within the tunnel 52, the wedge 116 will provide additional or increased compression in the distal end 136 as the interference screw 152 passes into the notched region 142. The plurality of teeth 122 having the perpendicular notches 128 provide a substantial surface engagement area to securely axially retain the four bundle graft 78 under proper tensioning endoscopically. In addition, the enlarged surface area distributes the tensioning force more uniformly over the graft 78. Still further, by providing a substantially non-moving engagement member against the graft 78, this reduces the possibility that the graft 78 may be frayed, slip or cut.

Referring now to FIGS. 13-15, a proximal end 164 of a wedge 166 according to the teachings of another embodiment of the present invention is shown. In this regard like reference numerals will be used to refer to similar structures. It should be noted that the distal end of the wedge 166 is the same as the distal end 136 of wedge 116 and the only modification here is to the proximal end 164. In this regard, the proximal end 164 does not include a pair of wings 144 but includes or defines a pair of notched regions 168 which are operable to be engaged by an endotibial plate grasper 172, shown in FIG. 16, and further discussed herein. The notches or grasper slots 168 are V-shaped and defined by a bevelled or rounded end 170 of the wedge 166.

The endotibial plate grasper 172 includes complementary tines or tips 174 which engage the notches 168 to firmly grasp and secure the plate 176. Set back from the tips 174 and adjacent thereto is an alignment plate 176 sized to be larger than the tibial tunnel 52 and angled substantially similar to the wings 144. The plate grasper or instrument 172 further includes a handle 178 having a locking mechanism 180 such that the plate 166 can be engaged by the tips 174 and locked or held secured by the locking mechanism 180.

Figure 17:
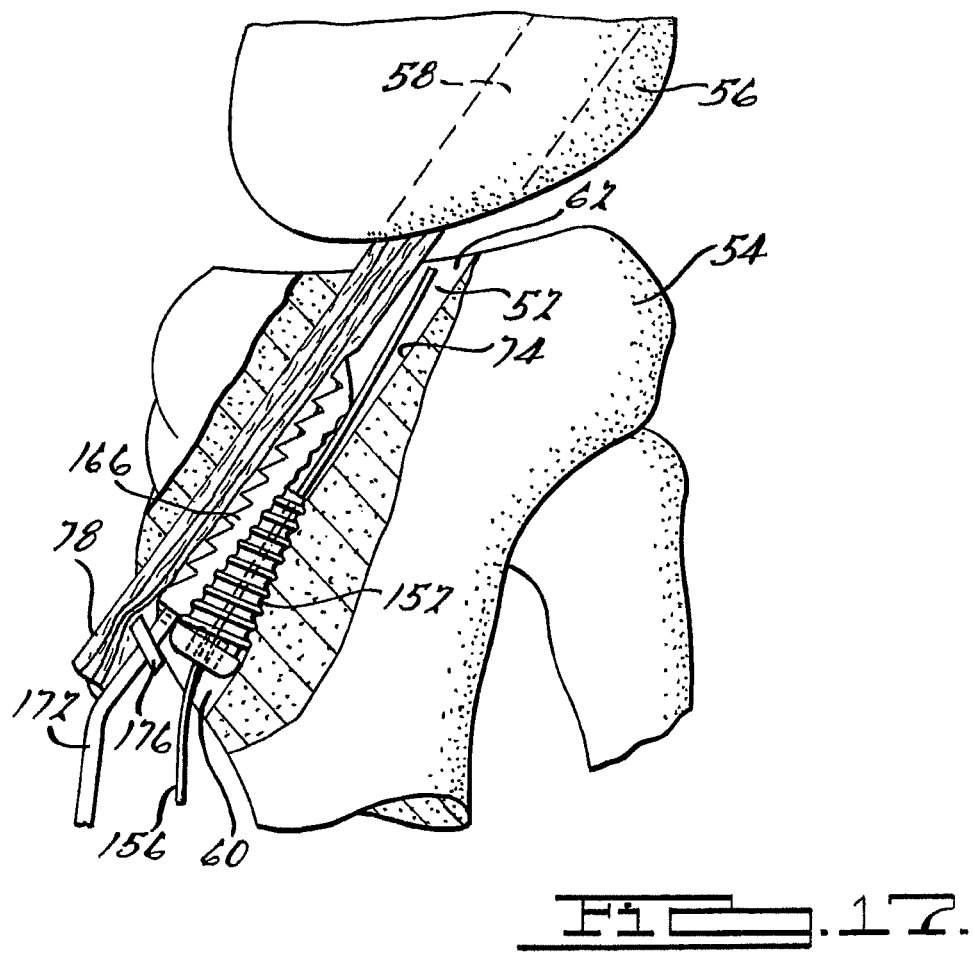
FIG. 17 is a side cross-sectional view illustrating a method for positioning the tibial fixation apparatus of FIG. 13 employing the instrument of FIG. 16.

The method for utilizing the wedge 166 in combination with the plate grasper 172 will now be described with reference to FIG. 17. Once again, the soft tissue grafts are harvested and prepared using known techniques. The tibial tunnel 52 and the femoral tunnel 58 are bored through both the tibia 54 and the femur 56. The four bundle graft 78 is again secured within the femoral tunnel 58 using known techniques such as the bone mulch screw identified above.

The four bundle graft 78 extending through the tibial tunnel 52 is then properly tensioned. Once the four bundle graft 78 is properly tensioned, the instrument 172 engages the notches 168 of the wedge 166, via the tips 174. With the wedge 166 being firmly held by the instrument 172, via the locking mechanism 180, the wedge 166 is axially inserted into the tibial tunnel 52 until the plates 176 engage the entrance opening 60 of the tibial tunnel 52. Here again, the teeth 122 transversely engage the four bundle graft 78, as the interference screw 152 is axially driven into the tibial tunnel 52. The plate 176 prohibits the wedge 166 from being axially drawn into the tibial tunnel 52 by more than a predetermined amount thereby maintaining proper graft tensioning, as well as maintaining the proper alignment of the wedge 166 against the four bundle graft 78. Once the four bundle graft 78 is axially secured within the tibial tunnel 52, the plate grasper 172 is removed from the wedge 166, thereby providing a properly tensioned and endoscopically axially secured four bundle graft 78.

Figure 18:
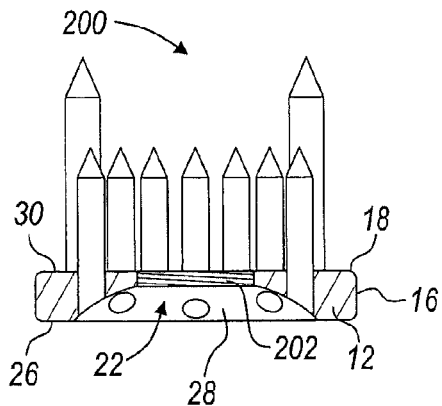
FIG. 18 is a side cross-sectional view of a tibial fixation apparatus according to the teachings of the preferred embodiment of the present invention.

Turning to FIG. 18, as well as referring to FIGS. 1-3, an apparatus 200 for tibial fixation of a soft tissue graft according to the teachings of a first preferred embodiment of the present invention is shown. The apparatus or washer 200 is substantially similar to the apparatus 10, as shown in FIGS. 1-3, and in this regard, like reference numerals will be used to identify like structures. Here again, the fixation apparatus or washer 200 includes the cylindrical body 12 and the plurality of spikes 14. The cylindrical body 12 includes the cylindrical sidewall 16 having the bevelled or rounded edges 18 and the substantially flat planar relief face 20 formed into a portion of the cylindrical sidewall 16. The body 12 further includes the internal bore 22 which includes a threaded internal sidewall 202 which is able to be threadably secured to a combination implant and guide instrument, further discussed herein. The top 26 of the body also includes the concentric counterbore 28 and the bottom 30 of the body 12 includes the plurality of spikes 14 extending out from the second side 30. Here again, the washer 200 may be made from any suitable bio-compatible material and may also be made in various different sizes, as with the washer 10, depending on the patient's needs and the doctor's requirements.

Figure 19:
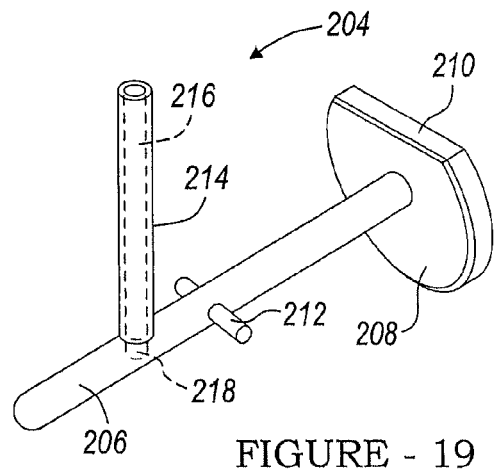
FIG. 19 is a perspective view of a counterbore guide used in preparing a counterbore to nestingly receive the tibial fixation apparatus of FIG. 18.

Referring to FIG. 19, a counterbore guide 204 is shown for use in preparing of a substantially perpendicular counterbore relative to a tibial tunnel formed in a tibia, further discussed herein. The counterbore guide 204 includes a substantially cylindrical body 206 having a circular handle 208 with a planar region 210. Extending substantially perpendicular from the cylindrical body 206 is a positioning bar 212 which is secured to the cylindrical body 206 by way of a groove formed in the lower portion of the cylindrical body 206 and a weld. The positioning bar 212 is utilized to engage the medial cortex of the tibia at two points to provide a predetermined insertion length of the counterbore guide 204 into the tibial tunnel. Set back from the positioning bar 212 is a tubular guide bushing 214. The guide bushing 214 includes a cylindrical bore 216 which mates and is concentric with a bore 218 defined by the cylindrical body 206. The guide bushing 214 is secured substantially perpendicular to the cylindrical body 206 by means of a weld or any other appropriate fixation. The guide bushing 214 engages the opening of the tibial tunnel and is operable to permit a guide bore to be formed substantially perpendicular to the tibial tunnel, further discussed herein.

Figure 20:
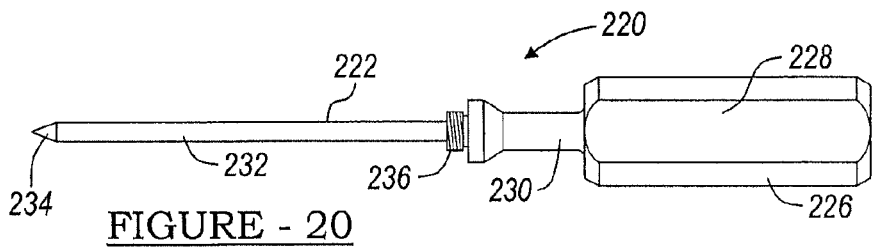
FIG. 20 is an elevational view of a first portion of a multi-purpose instrument.
Figure 21:
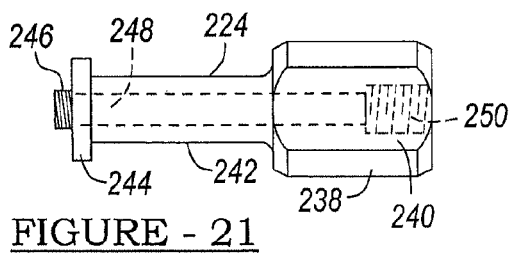
FIG. 21 is an elevational view of a second portion of the multi-purpose instrument of FIG. 20.

A combination implant and guide instrument 220 which is operable to implant the washer 200, as well as perform other purposes, is shown in FIGS. 20 and 21. The instrument 220 includes a first awl portion 222 and a second guide portion 224. The first awl portion 222 includes a cylindrically shaped handle 226 having notched regions 228 and an elongated neck 230. Extending substantially concentric with the handle 226 is an elongated cylindrical awl or guide shaft 232 having a distal point or tip 234. The first portion 222 also includes a threaded connector member 236 which is operable to threadably engage the second portion 224, further discussed herein.

The second guide portion 224 also includes a substantially cylindrical handle 238 having notches 240 and an elongated neck 242. Extending from the substantially cylindrical neck 242 is a circular impact plate 244. The impact plate 244 may either be formed integrally with the guide member 224 or may be formed as a separate annular member having an internal threaded bore which is threadably received upon a threaded connection member 246. The threaded connection member 246 extends out beyond the impact plate 244 and is operable to threadably engage threaded sidewall 202 of the fixation apparatus 200, further discussed herein. Passing concentrically through the drill guide 224 is a centerbore 248 having an internal threaded sidewall portion 250. The bore 248 is operable to receive the guide shaft 232, while the threaded sidewall 250 threadably engages the threaded connection member 236. In this way, the first portion 222 and the second portion 224 form the combination implant and guide instrument 220 which is operable to perform several functions during the implantation procedure.

Turning to FIGS. 22A-22D, a first preferred method for tibial fixation of a soft tissue graft will now be described. In this regard, like reference numerals will be used to identify like structures, as described in the method set forth in FIGS. 5A-5E. Initially, soft tissue grafts are harvested and prepared using known techniques and as previously described. Once the soft tissue grafts have been harvested and prepared, tunnel or hole placement is performed, as also previously described. Specifically, the tibial tunnel or bore 52 is drilled through the tibia 54 and into the femur 56 creating the femoral tunnel 58.

Once the tibial tunnel 52 is bored through the tibia 54, the cylindrical body 206 of the counterbore guide 204 is axially slid into the entrance opening 60 of the tibial tunnel 52. The counterbore guide 204 is slidably advanced into the tibial tunnel 52 until the positioning bar 212 engages and is flush against the medial cortex of the tibial 54 along two contact points. This will align the guide bushing 214 substantially adjacent and in contact with the anterior edge 64 or superior portion of the entrance opening 60 of the tibial tunnel 52. This provides for a stable three point contact at the entrance opening 60 to the tibial tunnel 52. Additionally, the planar region 210 of the handle 208 acts as a site mechanism with the guide bushing 214 to insure proper rotation of the counterbore guide 204 in the tibial tunnel 52.

Once the counterbore guide 204 is properly positioned within the tibial tunnel 52 and held by the handle 208, the substantially three point contact should be made within the oval opening 60 by way of the positioning bar 212 and the guide bushing 214. This substantially aligns the guide bushing 214 substantially perpendicular to the tibial tunnel 52. Once aligned and set, the first portion 222 of the combination implant and guide instrument 220 is employed. In this regard, the awl or guide shaft 232 is slidably received within the bore 216 of the guide bushing 214 until the point 234 engages the posterior wall 74 of the tibial tunnel 52. Once engaged, the first portion 222 is impacted by striking the handle 226 with a mallet or other appropriate impact device. The shaft 232 is impacted until the tip 234 is substantially adjacent to the posterior side of the tibia 54. This forms a guide bore 254 used to guide the combination implant and guide instrument 220 and a counterbore bit, further discussed herein. Once the guide bore 254 is formed, the guide shaft 232 is removed from the guide bushing 214 and the counterbore guide 204 is slidably removed from the tibial tunnel 52. This provides a substantially perpendicular guide bore 254 relative to the tibial tunnel 52.

Figure 22A:
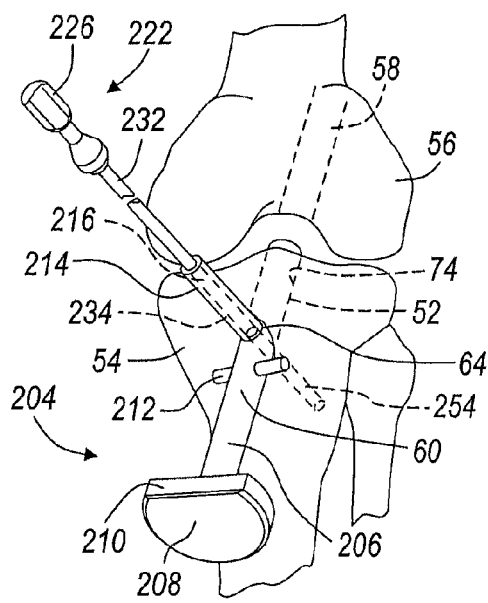
FIGS. 22A-22D illustrates a first preferred method for attaching a soft tissue graft using the tibial fixation apparatus according to the teachings of the preferred embodiment of the present invention.
Figure 22B:
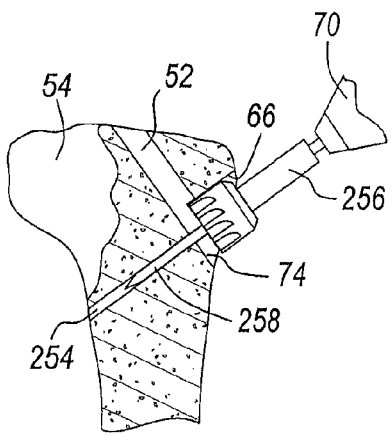
Figure 22C:
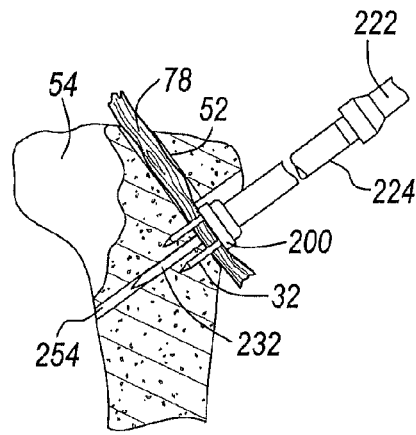
Figure 22D:
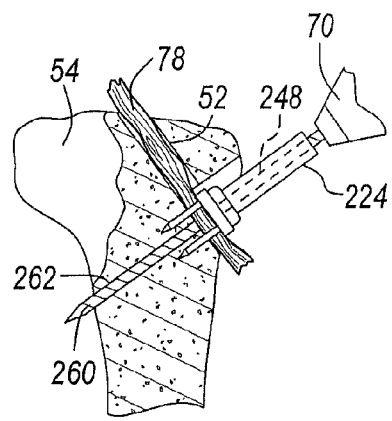

After the guide bore 254 is formed with the punch 222, the counterbore 66 is formed substantially perpendicular to the tibial tunnel 52 using a counterbore bit 256 and the drive mechanism 70, as shown in FIG. 22B. The counterbore bit 256 includes a substantially cylindrical centering nose 258 which rotatably engages the guide bore 254. Here again, the counterbore 66 is preferably bored to remove the anterior edge 64 or the superior portion of the entrance opening 60 to provide a substantially perpendicular counterbore 66. In other words, with the guide or centering nose 258 guided, via the guide bore 254, the counterbore bit 256 is perpendicular to the posterior wall 74 of the tibial tunnel 52 and is advanced to the posterior wall 74.

Once the counterbore 66 has been formed utilizing the counterbore bit 256, the four bundle graft 78 is first secured within the femoral tunnel 58 of the femur 56 using one of the many techniques known in the art and as previously described herein. Once the graft 78 is secured within the femoral tunnel 58, the graft 78 extends out through the tibial tunnel 52. The second portion 224 of the combination implant and guide instrument 220 is then threadably secured to the first portion 222 by way of the threaded sidewall 250 and the threaded connection member 236. Once assembled, the shaft 232 extends out beyond the impact plate 244 by about 1.25 inches. The threaded connection member 246 is then threadably engaged with the threaded sidewall 202 of the apparatus 200 to removably secure the apparatus 200 to the impact plate 244. As the apparatus 200 is threadably secured to the threaded member 246, the impact plate 244 seats within the spherical counterbore 28 and the shaft 232 extends out the center of the fixation apparatus 200.

The shaft 232 also extends out beyond the spikes 32 to permit guiding of the apparatus 200 substantially perpendicular to the tibial tunnel 52. Specifically, the planar relief face 20 of the apparatus 200 is first positioned inferior to the counterbore 66. The shaft 232 is then slidably engaged within the guide bore 254 until the spikes 32 engage the posterior portion 74 of the tibial tunnel 52. At this point, the graft 78 is oriented, as shown in FIG. 5E where the two grafts 94 and 96 of four bundle graft 78 pass along a first side of the shaft 232 and two grafts 98 and 100 pass along a second side of the shaft 232 such that each pair of grafts are positioned or guided between the longer guide spikes 32 and the guide shaft 232.

Here again, the fixation apparatus 200 is initially engaged with only the guide spikes 32 penetrating cancellous bone of the tibia 54 with the relief face 20 directed toward the entrance opening 60. Once the guide spikes 32 engage the tibial 54, the four bundle graft 78 is appropriately tensioned by pulling the four bundle graft 78 under the engagement spikes 36 within the counterbore 66 and out the area 102 defined by the relief 20 (see FIG. 5E) without binding on the sidewall 16 or the counterbore 66. Once proper tension is achieved on the four bundle graft 78, the apparatus 200 is fully implanted or nested within the counterbore 66 by striking the handle 226 with a mallet or other appropriate driving device, as shown clearly in FIG. 22C. Upon seating the apparatus 200, the engagement spikes 36 penetrate the two grafts 94 and 96 on the first side of the guide shaft 232 at multiple sights and the two grafts 98 and 100 on the second side of the guide shaft 232 to maintain the proper tensioning of the four bundle graft 78. This seats the fixation apparatus 200 flushly within the counterbore 66, thereby eliminating any objects extending out beyond the tibia 54.

Once the apparatus 200 is fully nested within the counterbore 66 or the posterior wall 74 of the tibial tunnel 52, the first portion 222 of the combination implant and guide instrument 220 is threadably disengaged from the second portion 224. With the second portion 224 still threadably secured to the apparatus 200, this provides a guide substantially perpendicular to the tibial tunnel 52, via the bore 248, passing through the second portion 224. A drill bit 260 driven by the driver 70 is then guided through the bore 248, between the grafts 94 and 96 and 98 and 100 and down through the guide bore 254, shown in FIG. 22D. The drill bit 260 enlarges the guide bore 254 for receipt of the low profile compression screw 108, shown in FIG. 5D. Once the bore 262 is drilled into the tibia 54 to the posterior cortex region, the bore 262 may then be tapped with an appropriate tap, should this be desired. The length of the screw 108 is then determined using any conventional measuring instrument. Once selected, the low profile compression screw 108 is passed through the apparatus 200 and threaded into the bore 262 to complete the fixation of the apparatus 200.

Figure 23:
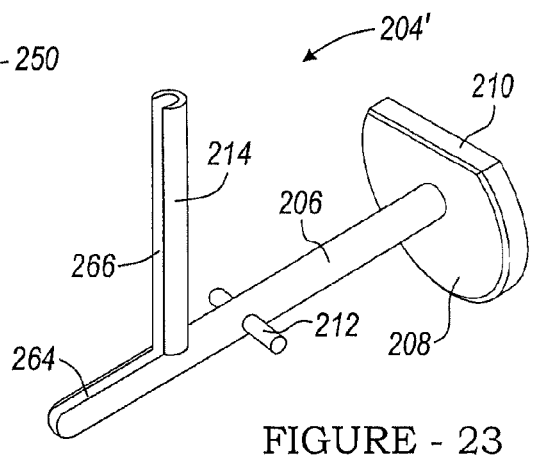
FIG. 23 is a perspective view of another counterbore guide used in preparing a counterbore to nestingly receive the tibial fixation apparatus of FIG. 18.

Referring now to FIG. 23, a second preferred embodiment of the counterbore guide 204N is shown. In this regard, like reference numerals will be used to identify like structures with respect to the counterbore guide 204. The counterbore guide 204N is substantially the same as the counterbore guide 204, except that the counterbore guide 204N includes or defines a slot 264 passing through the cylindrical body 206 and a slot 266 passing through the guide bushing 214. Each slot 264 and 266 enables a guide wire, further discussed herein, to be slidably passed through each slot and out from the counterbore guide 204N.

Figure 24:
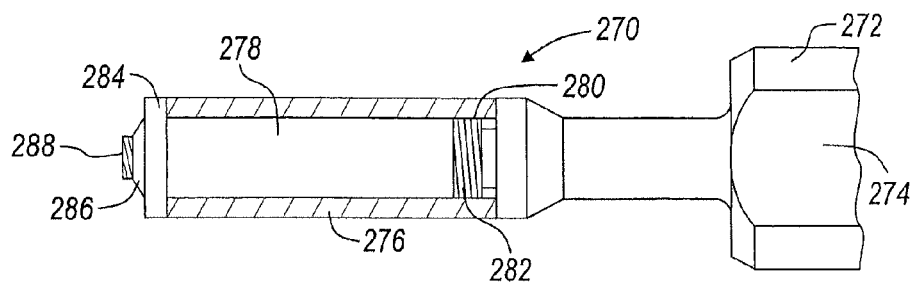
FIG. 24 is an elevational view of another multi-purpose instrument.

A second combination implant and guide instrument 270 according to the teachings of a second preferred embodiment of the present invention is shown in FIG. 24, which may be used in place of the instrument 220. The instrument 270 includes a substantially cylindrical handle 272 having notches 274 and an elongated tubular shaft 276. The shaft 276 defines a substantially cylindrical bore 278 passing axially through the shaft 276. The bore 278 includes a threaded sidewall portion 280 which is operable to be threadably engaged by a threaded connector member 282 extending from the handle 272. Positioned at the end of the shaft 276 opposite the handle 272 is a circular impact head or plate 284 having a substantially spherical impact face 286 and a threaded connection member 288. The implant plate 284 may be a separate member threaded on the connection member 288 or integral with the shaft 276. The connection member 288 threadably engages the threaded sidewall 202 of the apparatus 200, while the spherical face 286 nestingly rests within the counterbore 28.

Figure 25A:
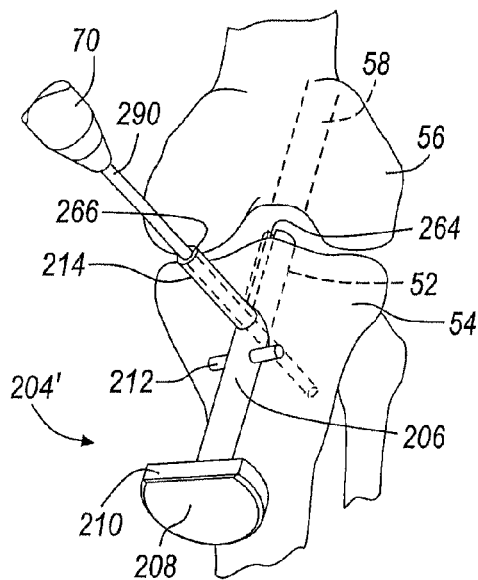
FIGS. 25A-25C illustrates a second preferred method for attaching a soft tissue graft using the tibial fixation apparatus according to the teachings of the preferred embodiment of the present invention.
Figure 25B:
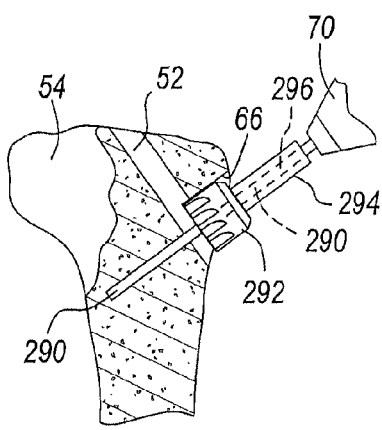
Figure 25C:
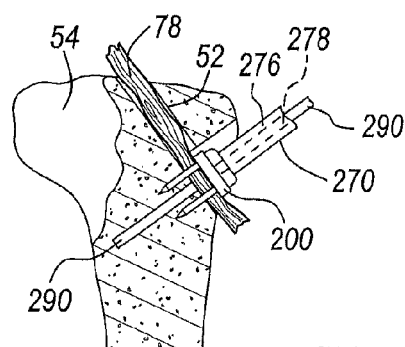

A second preferred method for tibial fixation of a soft tissue graft which employs the counterbore guide 204N and the combination implant and guide instrument 270 is shown in FIGS. 25A-25C. Here again, like reference numerals will be used to identify like structures. Once the graft 78 has been harvested and prepared using the known techniques, the tibial tunnel 52 is again drilled through the tibia 54 and into the femur 56 to form the femoral tunnel 58. As shown in FIG. 25A, the counterbore guide 204N is axially slid into the entrance opening 60 of the tibial tunnel 52 with the positioning bar 212 and the guide bushing 214 coming to rest against the opening 60. Once properly positioned, a conventional guide wire 290 is passed through the guide bushing 214 and fixedly driven into the tibia 54, via the driver 70 to create a guide box that secures the guide wire 290. Once secured to the tibia 54, the counterbore guide 204N is slidably removed from the tibial tunnel 52 as the guide wire 290 remains in place substantially perpendicular to the tibial tunnel 52. As the counterbore guide 204N is slidably removed from the tibial tunnel 52, the guide wire 290 exits through the slots 266 and 264, respectively.

The counterbore 66 is again formed by the use of a counterbore bit 292 which is driven by the driver 70. The counterbore bit 292 includes an elongated shaft 294 and includes and defines a cylindrical bore 296 passing through the entire counterbore bit 292. To insure that the counterbore bit 292 is aligned substantially perpendicular to the tibial tunnel 52, the counterbore bit 292 is slidably inserted over the guide wire 290 and rotatably advanced to form the counterbore 66, shown clearly in 25B, as the guide wire 290 passes up through the counterbore bit 292.

Once the counterbore 66 is formed, the combination implant and guide instrument 270 threadably receives the apparatus 200, via the threaded sidewall 202 and the threaded connector member 288. The impact face 284 nestingly seats within the counterbore 28 as the apparatus 200 threadably engages the threaded connector member 288. The apparatus 200 is again aligned substantially perpendicular to the tibial tunnel 52 by means of the guide wire 290. In this regard, the guide wire 290 extends through the apparatus 200 and into the bore 278 of the instrument 270 so that the instrument 270 is slidably guided by the guide wire 290 substantially perpendicular to the tibial tunnel 52. Here again, the spikes 32 are first set in the posterior wall 74 of the tibial tunnel 52 with the planar face 20 facing inferiorly. The graft 78 is again tensioned as previously described and the apparatus 200 is then fully seated by impacting the handle 272 with a mallet or other appropriate device.

Once the apparatus 200 is fully seated within the counterbore 66, the handle 274 is threadably removed from the shaft 276, via the threaded connector member 282, thereby exposing the bore 278. With the drill guide shaft 276 still threadably secured to the apparatus 200, the bore 278 guides the drill bit 260 driven by the driver 70, as shown similarly in FIG. 22D to form the enlarged bore 262. The low profile compression screw 108 is then inserted into the bore 262 to complete the fixation of the apparatus 200 within the counterbore 66.

The combination implant and guide instrument 220 performs at least three functions consisting of forming the guide bore 254, implanting the fixation apparatus 200 and guiding the drill bit 260. The combination implant and guide instrument 270 performs at least two functions including implanting the fixation apparatus 200 and guiding the drill bit 260. Accordingly, use of the combination implant and guide instrument 220 or 270 reduces the amount of separate instrumentation required to secure the soft tissue graft 78, as well as reduces or eliminates additional steps in the technique. Additionally, by maintaining one portion of each instrument 220 or 270 secured to the fixation apparatus 200 during the implant procedure, further accuracy is achieved. Further accuracy is also achieved by use of the guide shaft 232 or the guide wire 290 to maintain and form the counterbore 66 substantially perpendicular to the tibial tunnel 52, as well as insure that the apparatus 200 is impacted substantially perpendicular to the tibial tunnel 52.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A method of positioning an implant member relative to an anatomy, the method comprising: forming a bore in a bone of the anatomy;
   providing a first member extending between a first end and a second end;
   forming a graft to replace a soft tissue;
   positioning the formed graft in the bore;
   tensioning the formed graft within the formed bore;
   moving the first member axially, along the same direction of the graft, into the formed bore to a first position and engaging the graft with the graft tensioned;
   contacting an outer surface of the bone near the bore with a wing of the first member;
   providing a second member;
   moving the second member into the formed bore along the first member;
   compressing the first member against the graft within the formed bore;
   compressing the graft against a wall of the formed bore; and
   holding the first member substantially in the first position relative to the formed bore with the wing.

2. The method of claim 1, wherein providing the first member includes providing the first member having a substantially rounded first end.

3. The method of claim 2, further comprising:
   forming a notch at the rounded first end.

4. The method of claim 3, further comprising:
   forming at least three notches substantially parallel to one another at the rounded first end.

5. The method of claim 1, wherein holding the first member substantially in the first position includes resisting an axial movement of the first member with the wing of the first member against the surface of the bone.

6. The method of claim 1, wherein providing a second member includes providing a screw.

7. The method of claim 1, wherein compressing a first member against the graft includes driving the second member relative to the first member to provide a radial force against the first member towards the graft within the formed bore.

8. The method of claim 1, wherein moving the first member into the formed bore to engage the graft and contacting a surface of the bone near the bore with the wing occurs prior to moving the second member into the bore.

9. The method of claim 1, wherein forming the graft includes harvesting a portion of at least one of the semitendinosus and the gracilis;
   wherein tensioning the formed graft includes applying a force to the formed graft out of the bore.

10. A method of positioning an implant member relative to an anatomy, the method comprising:
    forming a bore along an axis in a bone of the anatomy;
    forming a graft to replace a soft tissue of the anatomy;
    moving a first member axially, along a same direction of the graft, into the formed bore to a first position and engaging the formed graft along a length of the formed graft while the formed graft is tensioned along the axis through the formed bore;
    contacting an outer surface of the bone near the bore with a wing of the first member;
    moving a second member axially along the axis into the bore along the first member;
    compressing the first member against the formed graft;
    compressing the formed graft against a wall extending along the axis of the formed bore;
    holding the first member substantially in the first position with the wing contacting the outer surface of the bone.

11. The method of claim 10, further comprising:
    providing the first member to extend between a first end and a second end.

12. The method of claim 11, further comprising:
    providing the first end to be a first terminal end of the first member;
    wherein the wing extends laterally from the first terminal end.

13. The method of claim 12, wherein moving the second member includes moving at least a portion of the second member past the first terminal end of the first member and the wing into the formed bore.

14. The method of claim 13, further comprising:
    engaging the second member with a driver;

wherein moving the second member includes moving the second member with the driver that is engaging the second member.

15. The method of claim 14, further comprising:
positioning the formed graft in the formed bore; and
tensioning the formed graft within the formed bore.

16. The method of claim 15, wherein tensioning the formed graft within the formed bore precedes moving the first member into the formed bore;
wherein forming the graft to replace the soft tissue of the anatomy includes forming a four bundle graft.

17. A method of positioning an implant member relative to an anatomy, the method comprising:
providing a first apparatus for fixation of a soft tissue graft, including:
providing the first apparatus to extend from a first terminal end to a second terminal end,
providing at least a portion of the distance between the first terminal end and the second terminal end to have a wedge shape,
providing the first apparatus with a first side and a second side extending at least a portion of a distance between the first terminal end and the second terminal end, wherein the first side is opposite the second side,
providing a plurality of teeth on the first side, each tooth of the plurality of teeth defined by a first sidewall and a second sidewall,
providing the second side with a second apparatus interference face, and
providing near the first terminal end at least one wing to engage the anatomy; and
providing a second apparatus to engage the second side to urge the first side of the first apparatus against the soft tissue graft.

18. The method of claim 17, wherein providing near the first terminal end at least one wing includes, providing the wing at an angle and a size such that when the first apparatus is axially inserted into a bore in the anatomy a face of the at least one wing lies substantially flush on a surface of the anatomy to prevent the first apparatus from being axially moved into the bore more than a predetermined amount.

19. The method of claim 18, further comprising:
forming the bore in a bone of the anatomy;
forming the soft tissue graft to replace a soft tissue of the anatomy;
moving a first apparatus into the formed bore to a first position that is the predetermined amount into the bore and engaging the formed graft while the formed graft is tensioned through the formed bore;
contacting an outer surface of the bone near the bore with the wing of the first apparatus, wherein the surface is the outer surface of the bone;
moving the second apparatus into the bore along the first apparatus;
compressing the first apparatus against the formed graft;
compressing the formed graft against a wall of the formed bore; and
holding the first apparatus substantially in the first position with the wing contacting the outer surface of the bone.

20. The method of claim 17, further comprising:
providing at least one tooth of the plurality of teeth to have at least one first notch formed into the at least one tooth.

21. The method of claim 17, further comprising:
providing the second terminal end with a rounded nose.

22. The method of claim 17, further comprising:
providing at the second terminal end at least two notches extending substantially perpendicular to one another on the first side.

23. The method of claim 17, wherein the first sidewall is vertical and the second sidewall is angled.

24. The method of claim 17, wherein providing the first apparatus includes forming the first apparatus of a biocompatible material including at least one of titanium, stainless steel, titanium alloy, cobalt-chrome-molybdenum alloy, polymer, or resorbable polymer.

* * * * *